United States Patent
Heald et al.

(10) Patent No.: US 9,597,459 B2
(45) Date of Patent: Mar. 21, 2017

(54) DRIVE MECHANISM FOR A DRUG DELIVERY DEVICE

(71) Applicant: Sanofi-Aventis Deutschland GmbH, Frankfurt am Main (DE)

(72) Inventors: Michael Heald, Crewe (GB); Stephen David Butler, Staffordshire (GB); Mark Philip Horlock, Cheshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 13/952,915

(22) Filed: Jul. 29, 2013

(65) Prior Publication Data
US 2013/0324936 A1 Dec. 5, 2013

Related U.S. Application Data

(63) Continuation of application No. 13/702,821, filed as application No. PCT/EP2011/059576 on Jun. 9, 2011, now abandoned.

(30) Foreign Application Priority Data

Jun. 11, 2010 (EP) .................................. 10165648

(51) Int. Cl.
A61M 5/315 (2006.01)

(52) U.S. Cl.
CPC ........ *A61M 5/31543* (2013.01); *A61M 5/315* (2013.01)

(58) Field of Classification Search
CPC .......... A61M 2005/2086; A61M 5/315; A61M 5/31528; A61M 5/31526; A61M 16/0486;
(Continued)

(56) References Cited

U.S. PATENT DOCUMENTS 5,827,232 A 10/1998 Chanoch et al.
2005/0137571 A1* 6/2005 Hommann ........ A61M 5/31553
604/500

(Continued)

FOREIGN PATENT DOCUMENTS

EP 1923085 5/2008
WO 99/38554 8/1999

OTHER PUBLICATIONS

International Search Report for Int. App. No. PCT/EP2011/059576, completed Aug. 29, 2011.
(Continued)

*Primary Examiner* — Emily Schmidt
*Assistant Examiner* — William Frehe
(74) *Attorney, Agent, or Firm* — McDonnell Boehnen Hulbert & Berghoff LLP

(57) ABSTRACT

A drive mechanism for a drug delivery device is presented that can be switched between a normal operation mode and a reset mode. A piston rod is displaced in a distal direction to deliver a dose in a normal operation mode and is displaced in the proximal direction in a reset mode. The drive mechanism also has a drive member that is rotationally moveable with respect to the housing, wherein in the normal operation mode, the drive member is coupled with the piston rod so that rotational movement of the drive member in the rotation direction with respect to the housing is converted into movement of the piston rod in the distal direction with respect to the housing, and wherein, in the reset mode, the piston rod is decoupled from the drive member.

10 Claims, 11 Drawing Sheets

(58) Field of Classification Search
CPC .......... A61M 25/0026; A61M 25/0071; A61M 5/31533; A61M 5/31548; A61M 5/31563; A61M 5/31565; A61M 5/31576; A61M 5/31578; A61M 5/31583
USPC ........................ 604/207–211, 224, 228, 232
See application file for complete search history.

(56) References Cited

U.S. PATENT DOCUMENTS

| | | |
|---|---|---|
| 2006/0153693 A1 | 7/2006 | Fiechter et al. |
| 2007/0005021 A1* | 1/2007 | Kohlbrenner ......... A61M 5/315 604/208 |
| 2008/0097322 A1* | 4/2008 | Markussen ............. A61M 5/20 604/135 |

OTHER PUBLICATIONS

International Preliminary Report on Patentability for Int. App. No. PCT/EP2011/059576, mailed Dec. 27, 2012.

* cited by examiner

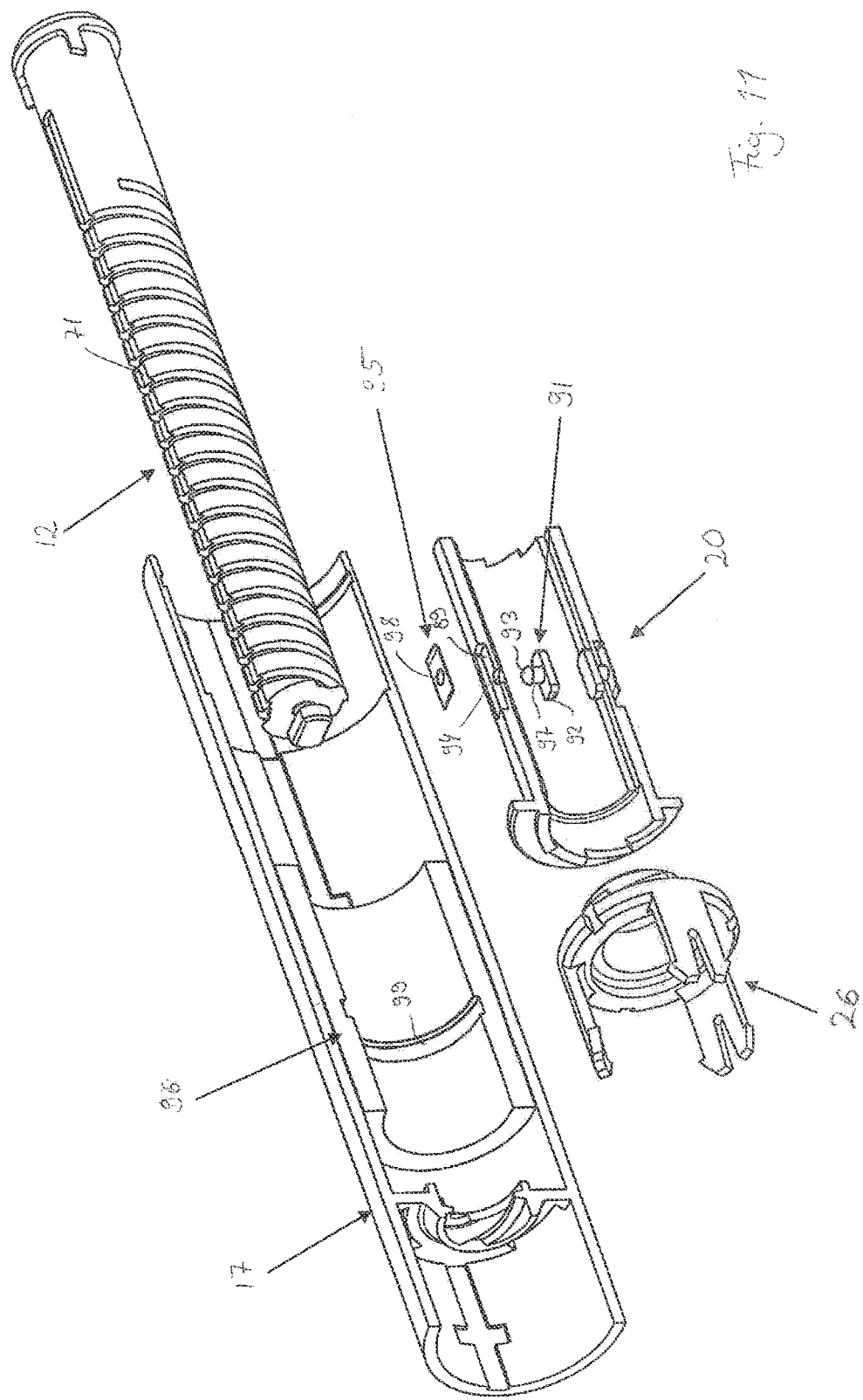

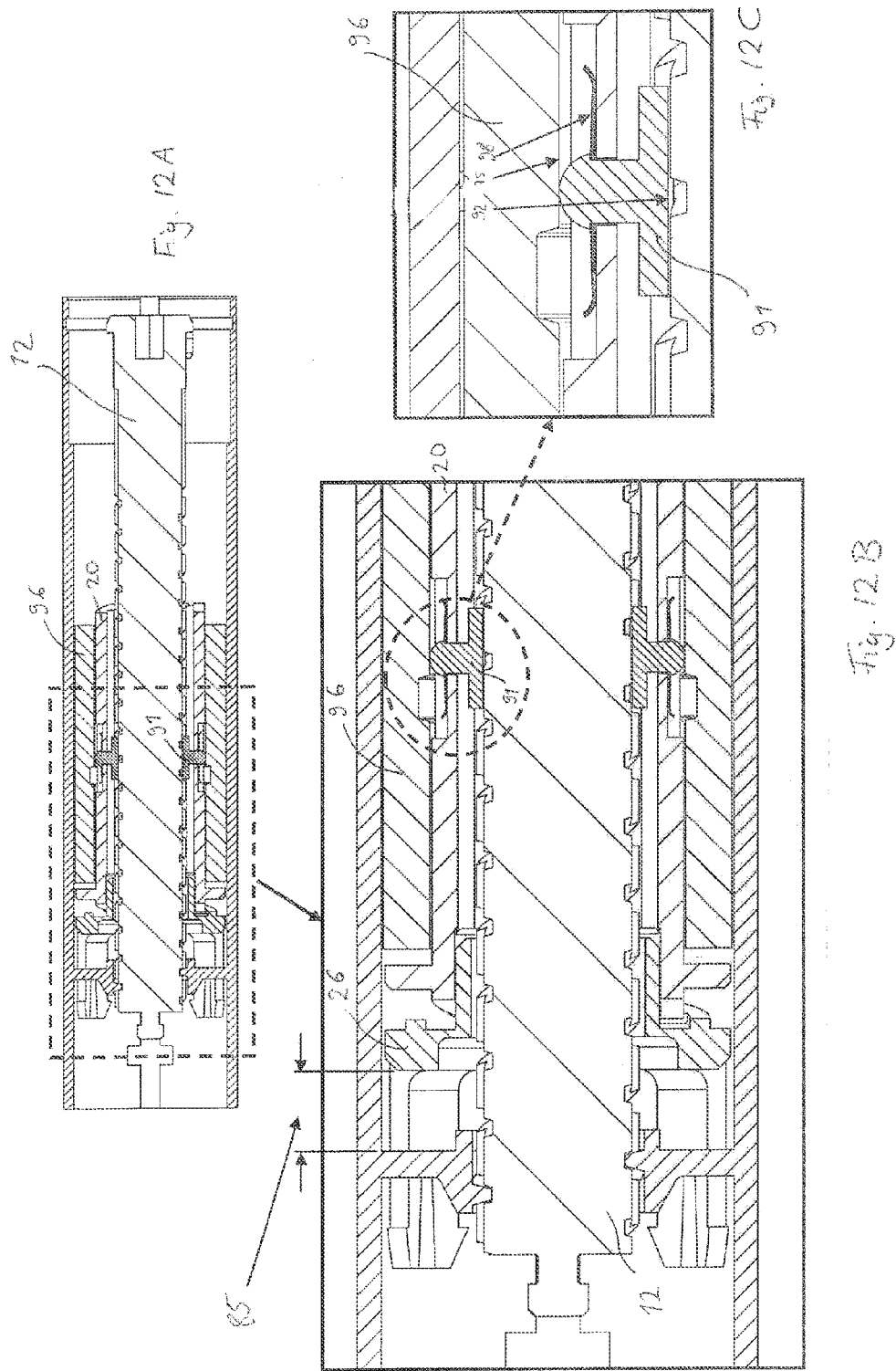

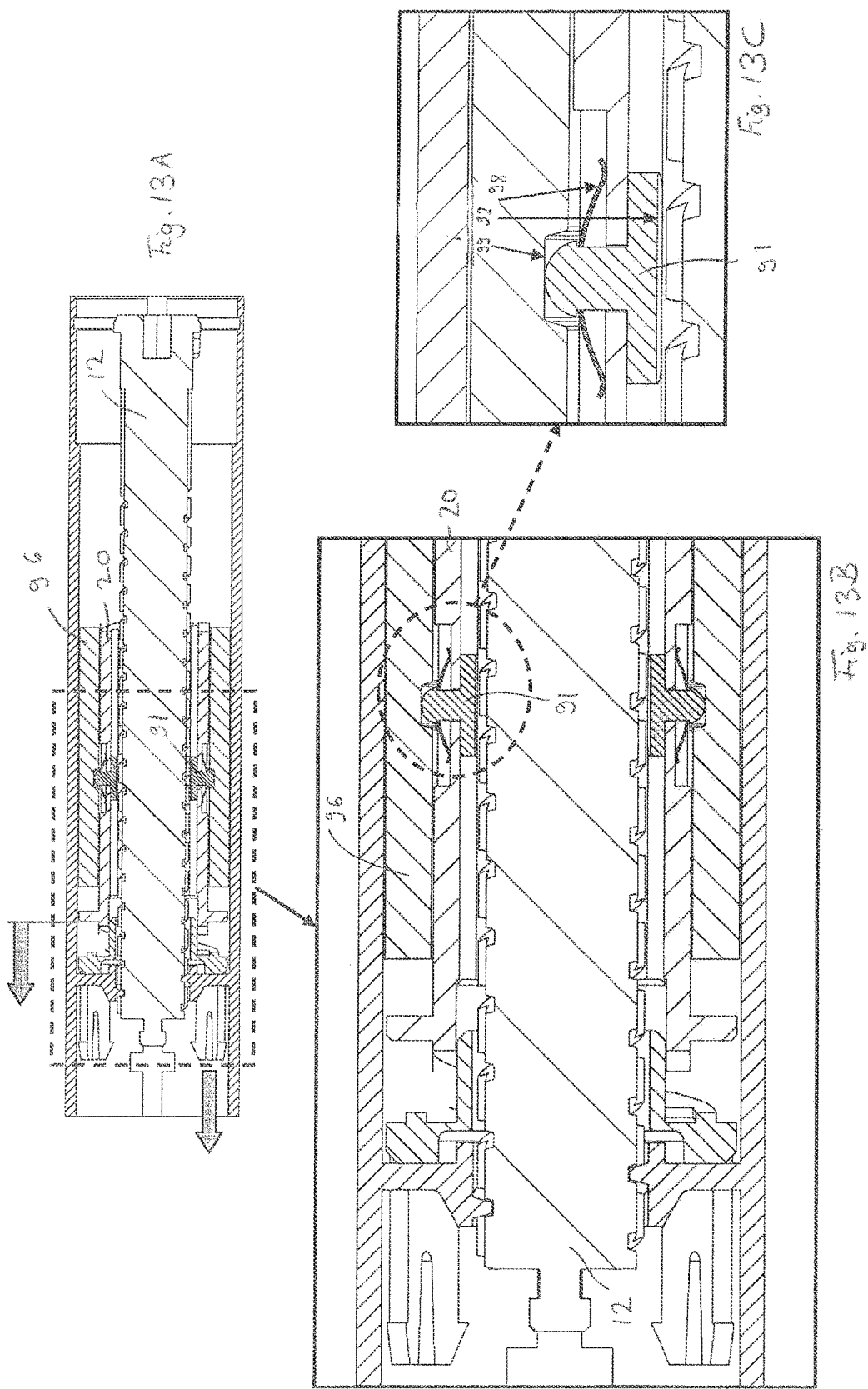

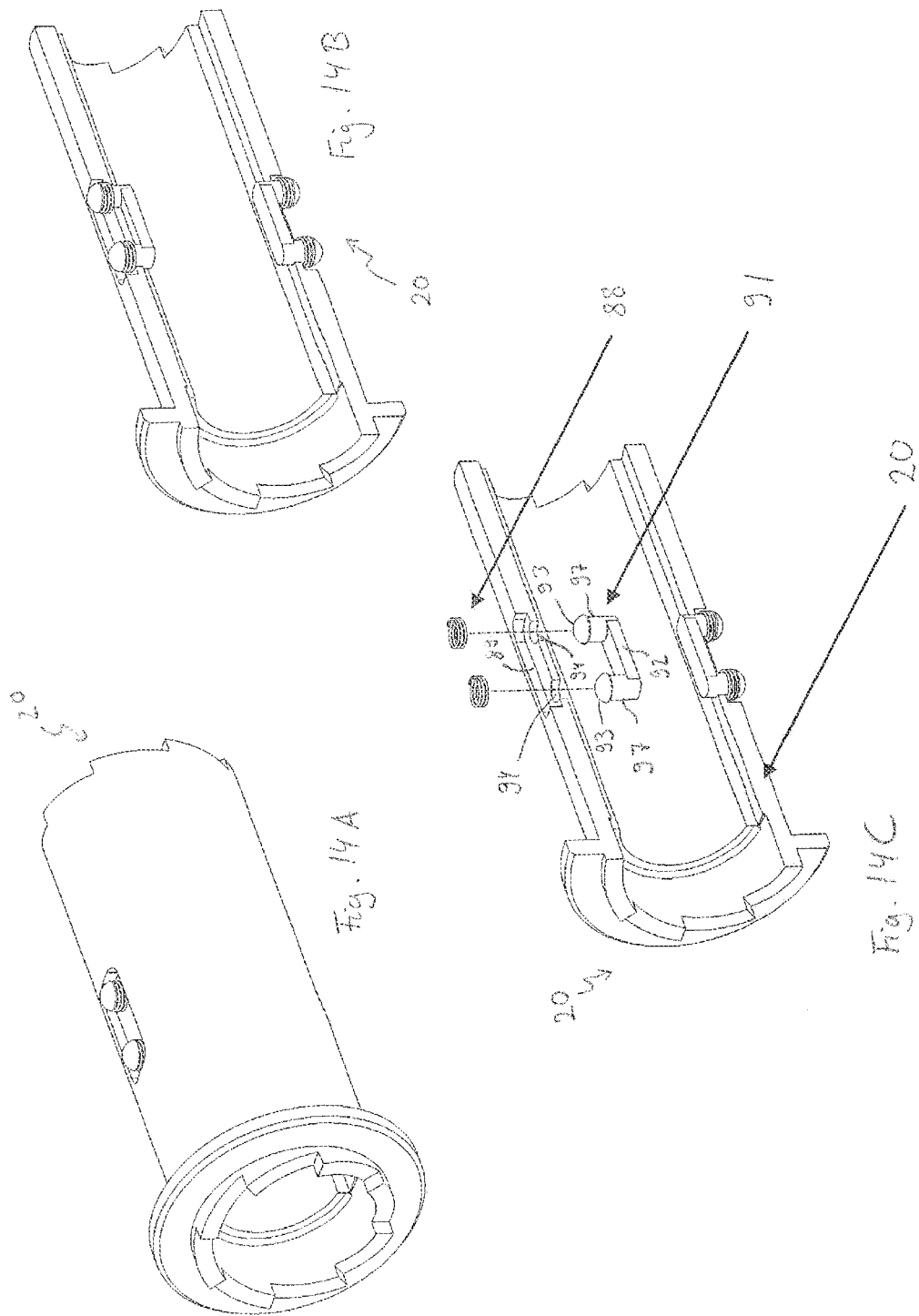

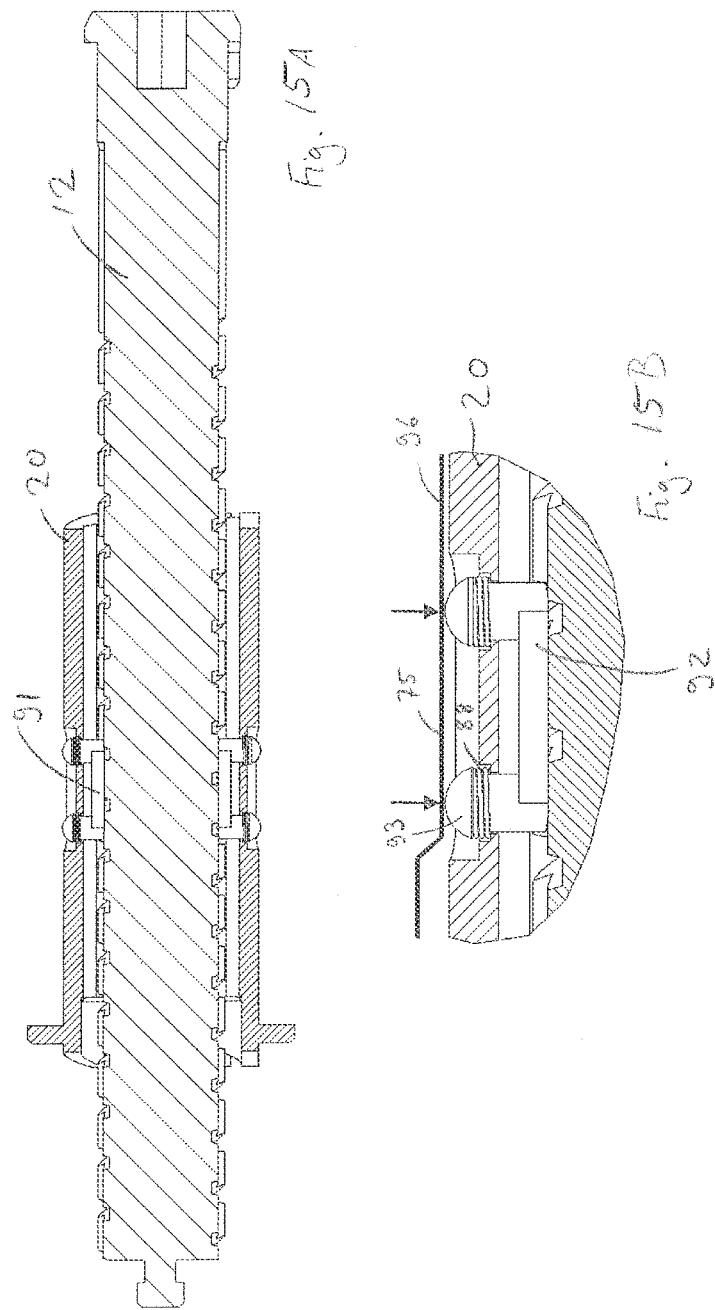

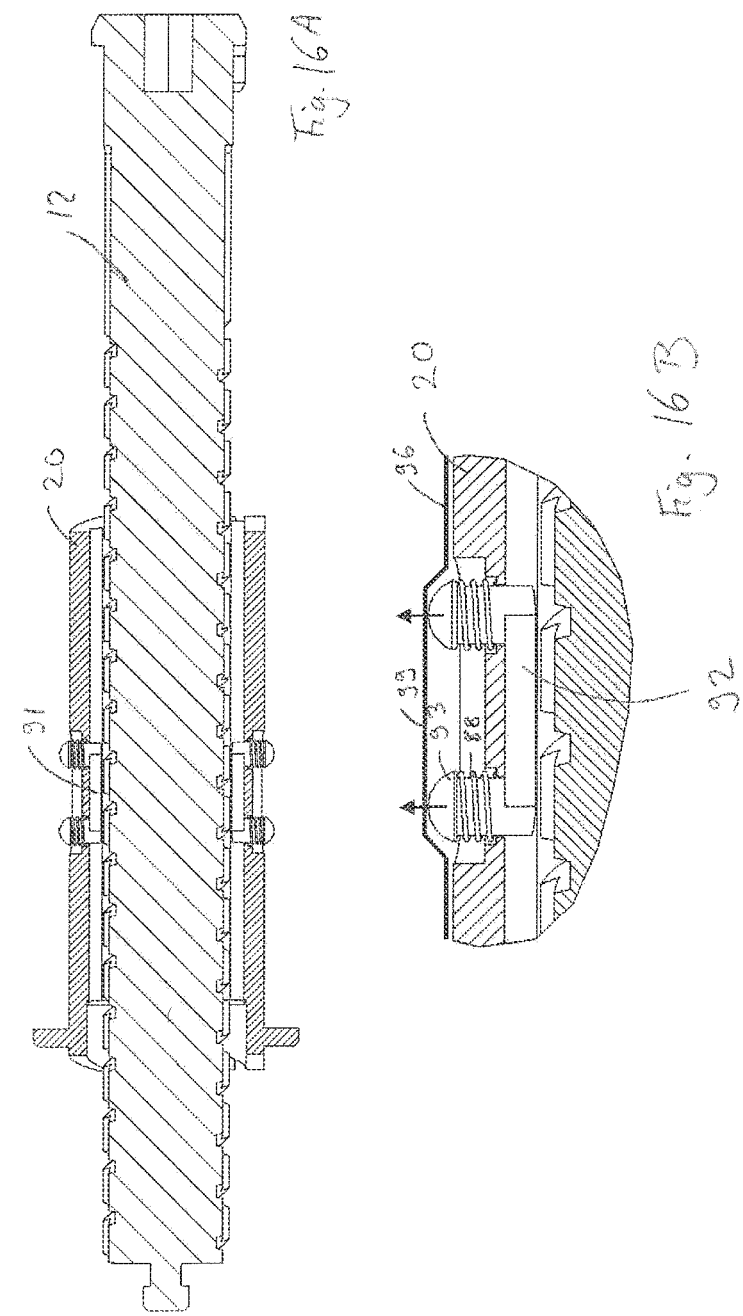

DRIVE MECHANISM FOR A DRUG DELIVERY DEVICE

CROSS REFERENCE TO RELATED APPLICATIONS

The present application is a continuation of U.S. patent application Ser. No. 12/702,821, filed Dec. 7, 2013, which is a U.S. National Phase Application pursuant to 35 U.S.C. §371 of International Application No. PCT/EP2011/059576 filed Jun. 9, 2011, which claims priority to European Patent Application No. 10165648.6 filed on Jun. 11, 2010. The entire disclosure contents of these applications are herewith incorporated by reference into the present application.

FIELD OF INVENTION

The invention concerns a drive mechanism for a drug delivery device.

BACKGROUND

In a drug delivery device, a piston within a cartridge that contains a drug may be displaced with respect to the cartridge in the distal direction by a piston rod which moves in the distal direction with respect to the cartridge.

A fixed dose pen injector is a device that can be used to inject a number of set dose sizes from a pre-filled cartridge which may be made of glass. This may be ideally suited for chronic daily therapies where repeat doses of the same size are regularly required. The device may be disposable or reusable.

SUMMARY

It is an aim of the invention to provide a drive mechanism which can be reset.

For achieving this aim a drive mechanism for a drug delivery device which can be switched between a normal operation mode and a reset mode is provided. The drive mechanism comprising:

a housing having a proximal end and a distal end, a piston rod which is adapted to be displaced in a distal direction with respect to the housing for delivering a dose in a normal operation mode of the drive mechanism, and which is adapted to be displaced in the proximal direction with respect to the housing in a reset mode of the drive mechanism, and a drive member which is rotationally moveable in a rotation direction with respect to the housing, wherein, in the normal operation mode, the drive member is coupled with the piston rod so that rotational movement of the drive member in the rotation direction with respect to the housing is converted into movement of the piston rod in the distal direction with respect to the housing, and wherein, in the reset mode, the piston rod is decoupled from the drive member.

This drive mechanism can be reset which enables to replace a cartridge after delivering all doses and replacing the cartridge by a new one containing a drug. During this change the drive mechanism must be reset. The device can be reset easily by the user. Moreover, the device is reusable, thus saving the environment.

In the normal operation mode, rotational movement in the rotation direction of the drive member with respect to the housing may be converted into rotational movement of the piston rod in the same direction, in the reset mode the piston rod being rotatable with respect to the drive member. In other words, in the reset mode the piston rod is decoupled from the drive member so that the piston can rotate in the proximal direction to an initial start position.

In one embodiment the drive member is splined to the piston rod in the normal operation mode. The drive member is unsplined to the piston rod in the reset mode. The splined connection is retractable, which means that the splines engage with the piston rod in the normal operation mode, the splines being disengaged from the piston rod in the reset mode.

An alternative embodiment of the drive mechanism operates in a different way. In the normal operation mode, rotational movement of the drive member with respect to the piston rod is converted into distal movement of the piston rod with respect to the housing, in the reset mode the piston rod being merely axially moved with respect to the drive member. The drive member is threadedly coupled with the piston rod in the normal operation mode. In the reset mode the drive member is not threadedly coupled any more, which may be achieved by separating the protrusions forming an outer thread of the threaded connection from tracks of the piston rod forming an inner thread of the threaded connection. This enables to axially shift the piston rod to its initial start position.

One embodiment of the drive mechanism is suitable for being releasably connected with a cartridge holder, wherein the drive mechanism is switched to the reset mode when the cartridge holder is detached from the drive mechanism. In other words, detaching and attaching the cartridge holder serves as a trigger for switching between the operation modes.

One embodiment of the drive member, which has an inner side facing the piston rod and an outer side facing away from the piston rod, comprises engagement means. In the normal operation mode the engagement means protrudes inwardly and engages with a track in the piston rod. In the reset mode the engagement means protrudes outwardly. The engagement means may be integrally formed with the drive member, e.g. a tongue-shaped part which can be pushed inwardly, thereby splining the drive member with the piston rod. Alternatively the engagement means may be formed as separate parts which are coupled to the drive member, e.g. a rivet-shaped engagement means which is moveable radially.

In one embodiment engagement means comprises a spring, the engagement means being biased outwardly. Preferably the drive member is decoupled from the piston rod in this position.

The drive mechanism may further comprise a push means which is moved to a position so that it pushes the engagement means inwardly when the drive mechanism is switched to the normal operation mode. In the reset mode the push means is moved away from the engagement means so that it moves outwardly. Alternatively, the drive mechanism comprises a push means, wherein the drive member is moved with respect to push means so that the push means pushes the engagement means inwardly when the drive mechanism is switched to the normal operation mode. In other words, the push means can be pushed towards the engagement means or the engagement means can be pushed towards the push means.

One embodiment of the engagement means is formed as a spring having a protruding element which engages the drive member and the piston rod in the normal operation mode, thereby splining the drive member to the piston rod. The protruding element is biased so that the drive member is rotatable with respect to the piston rod. The spring is deformable so that the protruding element locks the drive member and the piston rod in rotation.

In one embodiment the drive member has a track and the piston rod has a track. The protruding element engages with the tracks in the normal operation mode. The track of the drive member may be formed as a trench through which the protruding element may extend in the track of the piston rod.

In one embodiment a push means is provided which is moveable in a position so that it pushes the protruding element in the tracks of the drive member and the piston rod. The push member may push on the protruding element, thereby coupling the drive member with the piston rod.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further features, refinements and expediencies become apparent from the following description of the exemplary embodiments in connection with the figures.

BRIEF DESCRIPTION OF THE FIGURES

FIG. 11 shows an exploded view of a part of a further embodiment of the drive mechanism.

FIGS. 12A, 12B and 12C show sectional views of the embodiment of FIG. 11 in the normal operation mode.

FIGS. 13A, 13B and 13C show sectional views of the embodiment of FIG. 11 in the reset mode.

FIGS. 14A, 14B and 14C show different views of one embodiment of the drive member.

FIGS. 15A and 15B show sectional views of the embodiment of FIG. 14 and a piston rod in the normal operation mode.

FIGS. 16A and 16B show sectional views of the embodiment of FIG. 14 and the piston rod in the reset mode.

DETAILED DESCRIPTION

Figure 1:
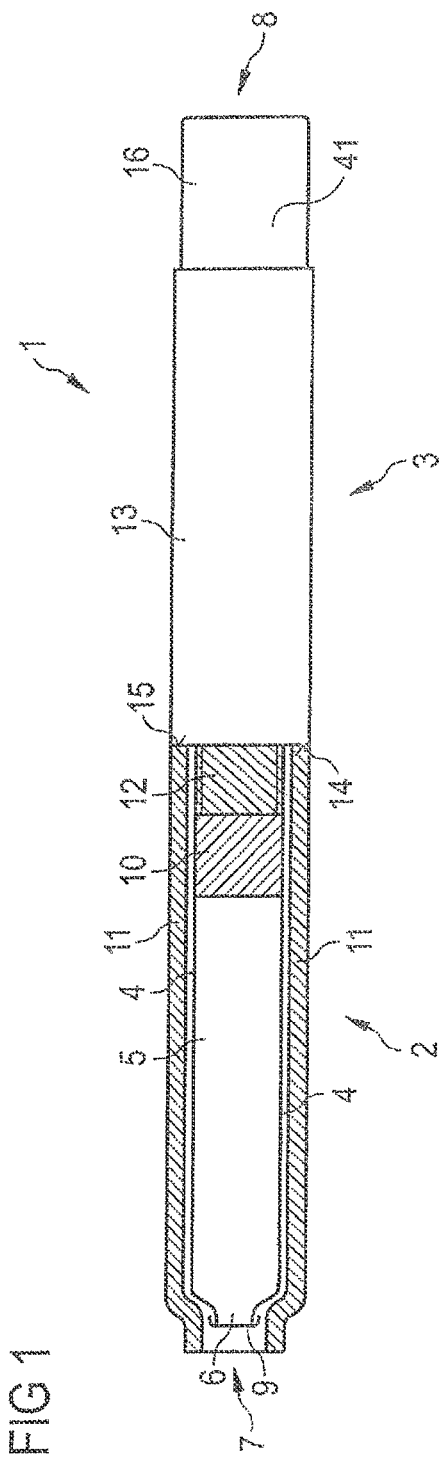
FIG. 1 schematically shows a partly sectional side view of an exemplary embodiment of a drug delivery device.

FIG. 1 shows a drug delivery device 1 which comprises a cartridge unit 2 and a drive unit 3. The cartridge unit 2 comprises a cartridge 4. Drug 5 is retained in the cartridge 4. The drug 5 is preferably liquid medication. The cartridge 4 preferably comprises a plurality of doses of the drug 5. The drug 5 may comprise insulin, heparin, or growth hormones, for example. The cartridge 4 has an outlet 6 at its distal end. Drug 5 can be dispensed from the cartridge through outlet 6. The device 1 may be a pen-type device, in particular a pen-type injector. The device 1 may be a disposable or a reusable device. The device 1 may be a device configured to dispense fixed doses of the medication or variable, preferably user-settable, doses. The device 1 may be a needle-based or a needle free device. The device 1 may be an injection device.

The term "distal end" of the drug delivery device 1 or a component thereof may refer to that end of the device or the component which is closest to the dispensing end of the device 1. The term "proximal end" of the drug delivery device 1 or a component thereof may refer to that end of the device or the component which is furthest away from the dispensing end of the device. In FIG. 1, the distal end of the device 1 was assigned reference numeral 7 and the proximal end of the device was assigned reference numeral 8.

The outlet 6 may be covered by a membrane 9, which protects medication 5 against external influences during storage of the cartridge. For drug delivery, membrane 9 may be opened, e.g. pierced. For example, membrane 9 may be pierced by a needle unit (not explicitly shown). The needle unit may be (releasably) attached to the distal end of the cartridge unit 2. The needle unit may provide for fluid communication from the inside of the cartridge 4 to the outside of the cartridge through outlet 6.

A piston 10 is retained within the cartridge 4. The piston 10 is movable with respect to the cartridge. The piston 10 may seal the drug 5 within the cartridge. The piston 10 expediently seals the interior of the cartridge 4 proximally. Movement of the piston 10 with respect to the cartridge 4 in the distal direction causes drug 5 to be dispensed from the cartridge through outlet 6 during operation of the device.

The cartridge unit 2 furthermore comprises a cartridge retaining member 11. The cartridge 4 is retained within the cartridge retaining member 11. The cartridge retaining member 11 may stabilize the cartridge 4 mechanically. Additionally or alternatively, the cartridge retaining member 11 may be provided with a fixing member (not explicitly shown) for attaching the cartridge unit 2 to the drive unit 3.

The cartridge unit 2 and the drive unit 3 are secured to one another, preferably releasably secured. A cartridge unit 2 which is releasably secured to the drive unit may be detached from the drive unit 3, for example in order to allow for providing for a new cartridge 4, if all of the doses of medication which once were in the cartridge formerly attached to the drive unit 3 have already been dispensed. The cartridge retaining member 11 may be releasably secured to the drive unit 3 via a thread, for example.

Alternatively, the cartridge retaining member 11 may be dispensed with. It is particularly expedient, in this case, to apply a robust cartridge 4 and to attach the cartridge directly to the drive unit 3.

The drive unit 3 is configured for transferring force, preferably user-exerted force, particularly preferably manually exerted force, to the piston 10 for displacing the piston 10 with respect to the cartridge 4 in the distal direction. A dose of medication may be dispensed from the cartridge in this way. The size of the delivered dose may be determined by the distance by which the piston 10 is displaced with respect to the cartridge 4 in the distal direction.

The drive unit 3 comprises a drive mechanism. The drive mechanism comprises a piston rod 12. The piston rod 12 may be configured for transferring force to the piston 10, thereby displacing the piston in the distal direction with respect to the cartridge 4. A distal end face of the piston rod 12 may be arranged to abut a proximal end face of the piston 10. A bearing member (not explicitly shown) may be arranged to advance the piston 10, preferably to abut the proximal end face of the piston 10. The bearing member may be arranged between piston 10 and piston rod 12. The bearing member may be fixed to the piston rod 12 or a separate member. If the piston rod 12 is configured to be rotated during operation of the device, for example during dose delivery, it is particularly expedient to provide for a bearing member. The bearing member may be displaced together with the (rotating) piston rod with respect to the housing. The piston rod may be rotatable with respect to the bearing member. In this way, the risk that the rotating piston rod drills into the piston and thereby damages the piston is reduced. Accordingly, while the piston rod rotates and is displaced with respect to the housing, the bearing member is preferably only displaced, i.e. does not rotate. The piston rod may be bounded by the bearing member.

The drive unit 3 comprises a housing 13 which may be part of the drive mechanism. The piston rod 12 may be retained in the housing. A proximal end side 14 of the cartridge unit 2 may be secured to the drive unit 3 at a distal end side 15 of the housing 13, for example via a threaded connection. Housing 13, cartridge 4 and/or cartridge retaining member 11 may have a tubular shape.

The term "housing" shall preferably mean any exterior housing ("main housing", "body", "shell") or interior housing ("insert", "inner body") which may have a unidirectional axial coupling to prevent proximal movement of specific components. The housing may be designed to enable the safe, correct, and comfortable handling of the medication delivery device or any of its mechanism. Usually, it is designed to house, fix, protect, guide, and/or engage with any of the inner components of the medication delivery device (e.g., the drive mechanism, cartridge, piston, piston rod), preferably by limiting the exposure to contaminants, such as liquid, dust, dirt etc. In general, the housing may be unitary or a multipart component of tubular or non-tubular shape.

The term "piston rod" shall preferably mean a component adapted to operate through/within the housing, which may be designed to transfer axial movement through/within the medication delivery device, preferably from the drive member to the piston, for example for the purpose of discharging/dispensing an injectable product. Said piston rod may be flexible or not. It may be a simple rod, a lead-screw, a rack and pinion system, a worm gear system, or the like. "Piston rod" shall further mean a component having a circular or non-circular cross-section. It may be made of any suitable material known by a person skilled in the art and may be of unitary or multipart construction.

The drive unit 3 comprises a dose part 16. The dose part 16 is movable with respect to the housing 13. The dose part 16 may be movable in the proximal direction with respect to the housing for setting of a dose of the drug 5 which is to be delivered and in the distal direction with respect to the housing for delivery of the set dose. The dose part 16 is preferably connected to the housing 13. The dose part 16 may be secured against rotational movement with respect to the housing. The dose part 16 may be moved (displaced) between a proximal end position and a distal end position with respect to the housing 13 (not explicitly shown). The distance by which the dose part is displaced with respect to the housing during setting of the dose may determine a size of the dose. The proximal end position and the distal end position may be determined by a respective stop feature which may limit the proximal or distal travel of the dose member with respect to the housing. The device 1 may be a variable dose device, i.e. a device configured for delivering doses of medication of different, preferably user-settable, sizes. Alternatively, the device may be a fixed dose device.

The device 1 may be a manually, in particular non-electrically, driven device. The (user-applied) force which causes the dose part 16 to be moved with respect to the housing 13 in the distal direction may be transferred to the piston rod 12 by the drive mechanism. For this purpose, other elements of the drive mechanism may be provided which are not explicitly shown in FIG. 1. The drive mechanism is preferably configured to not move the piston rod 12 with respect to the housing 13 when the dose part is moved in the proximal direction with respect to the housing for setting of the dose.

Embodiments of a drive mechanism which are suitable to be provided in the medication delivery device 1 as it was described above are described in more detail below.

An embodiment of a drive mechanism which is suitable for being implemented in the medication delivery device 1 as described above is described in connection with the following figures.

The drive mechanism comprises a housing part 17. The housing part 17 has a proximal end 18 and a distal end 19. The housing part 17 may be (outer) housing 13 of FIG. 1, a part thereof or an insert within housing 13, this insert is preferably secured against rotational and axial movement with respect to housing 13. The housing part 17 may be an insert sleeve, for example. The insert sleeve may be snap-fitted or glued to housing 13, for example. The housing part 17 may have a tubular shape. Housing part 17 may comprise outer fixing elements, for example snap-fit elements, for fixing housing part 17 to housing 13.

The piston rod 12 is retained in the housing 13, preferably within housing part 17. The piston rod 12 is driven in the distal direction with respect to the housing part 17 during dose delivery.

The drive mechanism furthermore comprises a drive member 20. Drive member 20 is retained within the housing part 17. Drive member 20 is configured to transfer force, preferably torque, to the piston rod 12. The transferred force may cause the piston rod 12 to be displaced in the distal direction with respect to the housing part 17 for dose delivery.

Drive member 20 is rotatable with respect to housing part 17. The drive member 20 may engage the piston rod 12. Rotational movement of the drive member, for example rotational movement in a second direction may be converted into distal movement of the piston rod 12 with respect to the housing part 17. This is explained in more detail below.

The drive mechanism furthermore comprises a rotation member 21. The rotation member 21 is rotatable with respect to the housing part 17 in a first direction, in particular for setting of a dose of the medication, and in a second direction, in particular for delivering the set dose. The second direction is opposite to the first direction. The first direction may be counter-clockwise and the second direction may be clockwise as seen from the proximal end of the device, for example.

Drive member, rotation member and/or piston rod are preferably configured to be rotatable about a (common) rotation axis. The rotation axis may extend through drive member, rotation member and/or piston rod. The rotation axis may be the main longitudinal axis of the piston rod. The rotation axis may run between the proximal end and the distal end of the housing part 17.

The rotation member 21 is coupled to the drive member 20 by a uni-directional clutch mechanism, in particular a friction clutch mechanism. This clutch mechanism permits rotational movement of the rotation member 21 with respect to the drive member 20 when the rotation member rotates in the first direction with respect to the housing part 17. The clutch mechanism prevents rotational movement of the rotation member 21 with respect to the drive member 20, when the rotation member rotates in the second direction with respect to the housing part 17. The drive member 20 may thus follow rotational movement of the rotation member 21 in the second direction with respect to the housing part 17.

The drive member 20 is arranged to abut and/or engage the rotation member and, in particular, engages rotation member 21. The drive member 20 comprises a toothing 22. Toothing 22 may be provided at one end of the drive member, e.g. its proximal end. The rotation member comprises a toothing 23. Toothings 22 and 23 face one another. Toothing 23 may be provided at one end of the rotation member which end faces the drive member 20, e.g. at the distal end of the rotation member. Toothing 22 comprises a plurality of teeth 24. Toothing 23 comprises a plurality of teeth 25. Teeth 24 and/or 25 may extend and preferably may be oriented along the rotation axis. Toothings 22 and 23 may be configured to mate with one another. The rotation member and the drive member may engage each other by toothings 22 and 23 being in engagement.

A respective tooth of teeth 24 and/or teeth 25 may be ramp-shaped, in particular along the azimuthal (angular) direction as seen from the rotation axis. The ramp of the respective tooth is limited (in the angular direction) by a steep end face of that tooth, i.e. a face of the tooth that runs parallel to the rotation axis or includes a smaller angle with the rotation axis when projected on this axis than the ramp when projected on this axis. The steep end face is followed by the ramp of the next tooth.

The teeth 24 may be circumferentially disposed on the drive member 20, particularly at the end of the drive member 20 which faces the rotation member 21. The teeth 25 may be circumferentially disposed on the rotation member 21, particularly at the end of the rotation member 21 which faces the drive member 20.

When the steep end faces of two teeth abut and the rotation member is rotated further on in the second direction, the steep sides stay in abutment and drive member 20 follows the rotation of rotation member 21. When the rotation member rotates in the first direction, the ramp of the teeth—which ramps, in particular, run obliquely with respect to the rotation axis—slide along each other and, in consequence, the rotation member 21 may rotate with respect to the drive member 20.

The drive mechanism furthermore comprises a stop member 26. The drive member may be arranged between the stop member 26 and the rotation member 21. The stop member 26 is configured for preventing rotational movement of the drive member 20 in the first direction with respect to the housing part 17 during setting of a dose, i.e. when the rotation member rotates in the first direction. Thus, the rotation member 21 may rotate in the first direction with respect to the housing part 17, whereas the drive member 20 and the stop member 26 do not rotate.

The stop member 26 is coupled to the drive member 20 by another uni-directional clutch mechanism, in particular a friction clutch mechanism. This clutch mechanism prevents rotational movement of the drive member 20 with respect to the stop member 26 when the rotation member 21 rotates in the first direction with respect to the housing part 17. The clutch mechanism permits rotational movement of the drive member 20 with respect to the stop member 26, when the rotation member 21 rotates in the second direction with respect to the housing part 17.

Thus, the rotation member 21 may rotate with respect to the drive member 20 and the stop member 26 in the first direction during setting of the dose, with rotation of the drive member 20 being prevented by its interaction with the stop member 26, and rotation member 21 as well as drive member 20 may rotate with respect to the stop member 26 in the second direction during delivery of the dose.

The stop member 26 may be arranged to abut and/or engage the drive member 20 during setting of the dose and, preferably, during delivery of the dose. The stop member 26 has a toothing 27. Toothing 27 may be provided at one end of the stop member which faces the drive member, e.g. its proximal end. The teeth may be ramp-shaped with a steep side and a less steep ramp. The teeth may be azimuthally disposed along the stop member, in particular on the perimeter of the stop member.

Drive member 20 has a toothing 28. Toothing 28 may be provided at one end of the drive member which faces the stop member, e.g. the distal end of the drive member. The teeth of toothing 28 may extend and preferably may be oriented along the rotation axis. Toothings 22 and 28 of the drive member 20 are oppositely disposed. Toothing 28 may be configured in accordance with toothing 21 of the rotation member. Toothing 22 may be configured in accordance with toothing 27 of the stop member. Toothings 27 and 28 may face one another. Toothings 27 and 28 may mate with one another. Toothings 27 and 28, in particular the steep sides of the teeth, do cooperate, e.g. abut, for preventing rotation of the drive member 20 with respect to the housing part 17 and, in particular, with respect to the stop member 26 in the first direction.

Stop member 26 is preferably secured against rotational movement, particularly preferably permanently secured against rotational movement, with respect to the housing part 17. Stop member 26 may be fixed to the housing or integrated into the housing. Stop member 26 may be fixed against displacement with respect to the housing part 17 or displacement with respect to the housing part 17 may be allowed.

Figure 2:
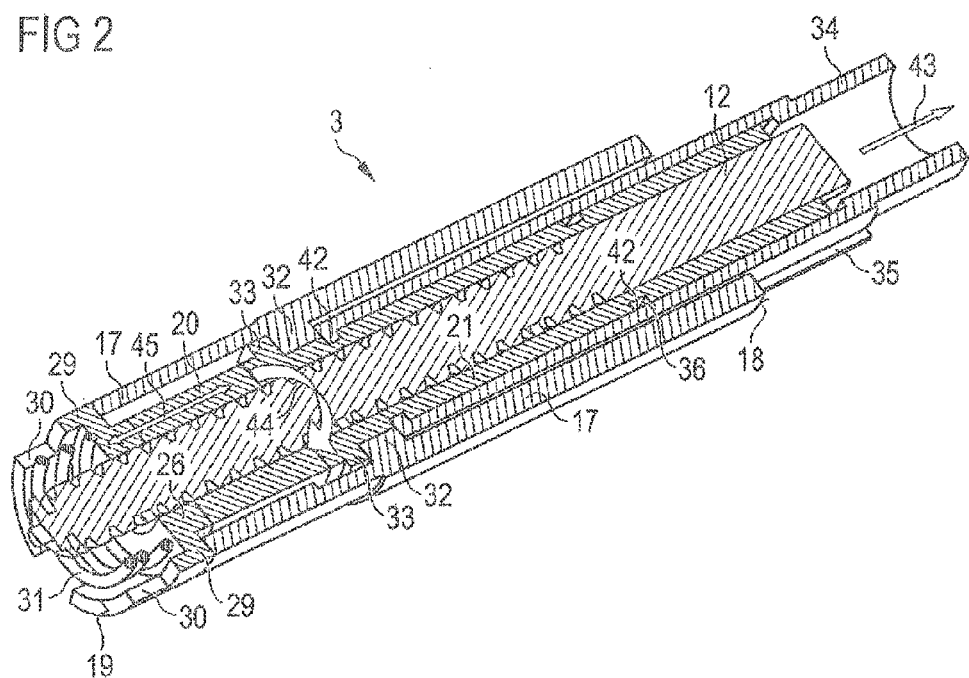
FIG. 2 schematically shows a perspective sectional view of a part of a drive mechanism according to a first embodiment with schematically indicated movements of elements thereof during setting of a dose.
Figure 3:
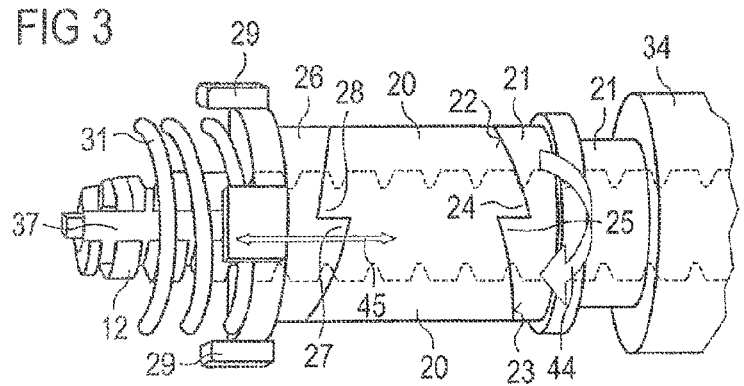
FIG. 3 schematically shows a more detailed side view of a part of FIG. 2.

As it is illustrated in the present embodiment, stop member 26 is displaceable with respect to the housing but non-rotatable with respect to the housing part 17. For that purpose, one or a plurality of, preferably oppositely disposed, guide features, for example guide lugs 29, are provided in the stop member 26. The respective guide feature 29 engages a corresponding guide slot 30 which may be provided in the housing, e.g. in housing part 17. This can be seen in FIGS. 2 to 3. A guide feature 29 cooperates with a guide slot 30 to prevent rotational movement of the stop member with respect to the housing part 17, with axial movement of the stop member 26 with respect to the housing being allowed. The axial movement of the stop member 26 may compensate for play between components of the drive mechanism during operation.

From the group comprising drive member 20, stop member 26 and rotation member 21 one or more members, preferably two members or three members, may be axially displaceable with respect to the housing part 17 and, preferably, with respect to the piston rod 12. Therein, the drive member and another one of the recited members may be axially displaceable with respect to the housing. The remaining member may be secured against axial displacement or may also be axially displaceable during operation of the drive mechanism for medication delivery. Accordingly, if the drive member and the stop member are axially displaceable, the rotation member may be axially secured or axially displaceable and so on. Play between the components caused by relative (axial) movement of components of the clutch mechanism with respect to the housing can be compensated for in this way. The distance by which the respective components may be axially displaced with respect to the housing may correspond to the (maximum) depth of a tooth of the respective toothing 22 or 28 of the drive member. Alternatively, the distance may be greater than the (maximum) depth of a tooth of the respective toothing.

Furthermore, the drive mechanism comprises a resilient member 31, preferably a spring member. The resilient member 31 may be biased during medication delivery operation of the drive mechanism. The resilient member may provide for a force that tends to keep the drive member 20 in engagement with the stop member 26 and/or the rotation member 21. The force may be exerted along the rotation axis. In the situation shown in FIGS. 2 to 3, this force may be exerted in the proximal direction. The resilient member 31 may be a helical (coil) spring. The resilient member 31 may be a compression spring.

The resilient member 31 may keep the drive member 20 and the stop member 26 in (permanent) mechanical contact, e.g. in abutment, with each other during setting and delivery of a dose of the medication. Alternatively or additionally, the resilient member 31 may keep the drive member 20 and the rotation member 26 in (permanent) mechanical contact, preferably abutment, with each other during setting and delivery of a dose of the medication.

The resilient member 31 may be integrated within stop member 26 or a separate component. The resilient member 31 may be arranged on the distal end side of the stop member 26.

The drive mechanism furthermore comprises a support member 32. Support member 32 is expediently fixed against axial and rotational movement with respect to the housing part 17 or integrated into housing part 17. Support member 32 is arranged on that side of the drive member 20 which is remote from the stop member 26. Support member 32 may be a protrusion, for example a ring-like protrusion. Rotation member 21 may extend through an opening in support member 32. The support member 32 may provide for a counter force to the force which is exerted by the resilient member 31. Permanent abutment of the rotation member with the drive member and of the drive member with the stop member during setting and delivery of medication is facilitated in this way.

The rotation member 21 has an (radially) outwardly protruding member 33, for example a flange portion. The protruding member 33 is expediently provided for abutting support member 32, in particular the distal end side of support member 32.

The drive mechanism furthermore comprises a dose member 34. Dose member 34 may be dose part 16 or may be a part of the dose part 16 of FIG. 1. Dose member 34 is movable with respect to the housing in the proximal direction for setting of a dose and for delivery of the dose. For example, the dose member 34 may be moved in the proximal direction with respect to the housing part 17 during dose setting and in the distal direction with respect to the housing part 17 during dose delivery. The dose member 34 may engage the housing part 17 or, alternatively, another part of housing 13 (not explicitly shown). Dose member 34 is preferably secured against rotational movement with respect to the housing part 17. The dose member 34 may comprise a guide feature 35, for example a guide lug or a guide slot, that engages another guide feature, for example a guide slot or a guide lug, respectively, that is provided in the housing part 17 or the housing 13. The dose member 34 may be displaced with respect to housing part 17 preferably only axially along and/or rotationally around the rotation axis.

Dose member 34 may be moved in the proximal direction and in the distal direction with respect to rotation member 21. Dose member 34 is arranged to be coupleable and is preferably (permanently) coupled to rotation member 21 such that movement of the dose member, e.g. in the proximal direction with respect to the housing part 17, for setting a dose of the medication is converted into rotational movement of the rotation member in the first direction and movement of the dose member, e.g. in the distal direction with respect to the housing part 17, for delivering the dose is converted into rotational movement of the rotation member 21 in the second direction opposite to the first direction.

The rotation member 21 may be provided with an (outer) thread 36. Thread 36 may be engaged with one of or a plurality of engagement members 42 of dose member 34. The respective engagement member may be arranged on the inside of the dose member. The respective engagement member may be a thread or a part of a thread, for example. Thus, dose member 34 and rotation member 21 may be threadedly coupled, in particularly threadedly engaged. The rotation member 21 may be arranged inside the dose member 21.

The rotation member 21, the drive member 20, the stop member 26 and/or the dose member 34 may be or may comprise a respective sleeve. The piston rod 12 may be arranged to be driven and, in particular, may be driven through one of, more of or all of those sleeves. The piston rod 12 may run through one of, more of or all of those sleeves.

The drive member 20 and the piston rod 12 are configured for rotational movement of the drive member 20 with respect to the housing being converted into rotational movement of the piston rod with respect to the housing. The drive member 20 may engage the piston rod 12. The piston rod 12 is displaceable with respect to the drive member 20 along a displacement axis. Presently, the displacement axis runs along the rotation axis. The drive member 20 may be splined to the piston rod 12, for example.

The piston rod 12 is threadedly coupled to the housing 13 and comprises an engagement track 37, preferably two oppositely disposed engagement tracks, on the outside. The (respective) engagement track 37 may interrupt the thread. The (respective) engagement track 37 preferably extends along the axis along which the piston rod is displaceable with respect to the housing and, in particular, with respect to the drive member.

Rotational movement of the drive member 20 with respect to the housing may thus be converted into rotational movement of the piston rod 12 with respect to the housing and the rotational movement of the piston rod 12 is, on account of the threaded engagement of the piston rod and the housing (part), converted into movement of the piston rod with respect to the housing in the distal direction.

The dose part 16 may comprise a dose knob which may be configured to be gripped by a user. Dose knob 41 may be arranged and connected to the dose member 34 at the proximal end. Dose knob and dose member may be unitary.

In the following, operation of the present drive mechanism for delivering drug from the cartridge 4 of FIG. 1 is described.

To set a dose, a user may manually move dose member 34 in the proximal direction (arrow 43) with respect to the housing part 17. To do so, the user may grip dose knob and pull it in the proximal direction. Dose member 34 moves proximally also with respect to the rotation member 21. Proximal movement of the rotation member is prevented by support member 32 which abuts protruding member 33 of rotation member 21. Consequently, the proximal movement of dose member 34 with respect to the housing part 17 is converted into rotational movement of the rotation member 21 in the first direction (arrow 44) with respect to the housing part 17, in particular on account of the threaded engagement of dose member 34 and rotation member 21. Thus, the rotation member 21 rotates in the first direction—counter-clockwise as seen from the proximal end of the rotation member—with respect to the housing. Rotation member 21 also rotates with respect to the drive member 20 and to the stop member 26. The drive member 20 is prevented from rotating in the first direction by interaction with the stop member 26, e.g. by interlocking of toothings 27 and 28. As the piston rod 12 is coupled to the drive member 20 and rotation in the first direction of the drive member would cause the piston rod to travel in the proximal direction, the piston rod 12 is prevented from being driven in the proximal direction by interaction of stop member 26 and drive member 20. By preventing the piston rod 12 from moving during dose setting dose accuracy can be increased.

When the rotation member 21 rotates in the first direction, the ramps of the teeth of toothing 23 of rotation member 21 slide along the ramps of the teeth of toothing 22. Thus, a tooth of the rotation member may index around the rotation axis until the tooth engages one of the next teeth of toothing 22 of drive member 20. The teeth of rotation member 21 slide along the ramps of the teeth of drive member 20. During this movement, drive member 20 and, in particular, stop member 26 are displaced along the rotation axis with respect to piston rod 12 and housing by a distance determined by, preferably equal to, the depth of a tooth of toothing 22, before a tooth of toothing 23 (totally) disengages that tooth of toothing 22. Afterwards, the tooth of the rotation member 21 engages the next tooth of toothing 22 and the force provided by resilient member 31 moves drive member 20 and, in particular, stop member 26 back along the rotation axis into the axial start position. An according movement of stop member and drive member in the distal direction and back into the proximal direction is indicated by double arrow 45 in FIGS. 2 and 3.

A tooth of the rotation member which engages the next tooth of the drive member may cause an audible and/or tactile feedback to the user.

The drive mechanism is suitable for a fixed dose device or a user settable dose device. The size of the fixed dose of medication which is to be delivered or the increments in which a user-settable dose may be varied by a user are preferably determined by the distribution of the teeth of the respective toothings in the drive member, rotation member and stop member. The rotation member may be rotated over more than one teeth (dose increment) of the drive member for a user-settable dose device and over one tooth (only) for a fixed dose device. The number of teeth in the drive member 20 over which the rotation member 21 rotates during dose setting determines the size of the dose which is actually delivered.

After the dose has been set, the dose part 16 and with it the dose member 34 is moved (pushed) by the user in the distal direction with respect to housing part 17. Thus, the dose member 34 is moved in the distal direction with respect to the housing part 17. The rotation member 21 accordingly rotates in the second direction, which is opposite to the first direction, with respect to the housing. Drive member 20 follows rotational movement of the rotation member in the second direction. Rotational movement of the drive member 20 in the second direction is converted into rotational movement of the piston rod 12 in the second direction, which movement, in turn, is converted into movement of the piston rod 12 in the distal direction. Accordingly, the piston 10 of FIG. 1 may be displaced in the distal direction with respect to the cartridge 4 and a dose of medication 5 is dispensed from the cartridge the amount of which corresponds to the previously set dose.

During dose delivery, toothings 22 and 23 interlock and ramps of the teeth of toothing 28 of the drive member 20 slide along ramps of the teeth of toothing 27 of stop member 26. This movement is similar to that as described above for the relative rotational movement of rotation member and drive member with opposite rotation direction. The stop member 26 is thereby displaced in the distal direction with respect to the drive member 20 by a distance corresponding to the depth of a tooth of toothing 27 in stop member 26. Resilient member 31 forces the stop member 26 back into the axial starting position, when the next tooth of toothing 28 is engaged by the respective tooth of toothing 27.

A tooth of the drive member which engages the next tooth of the stop member may cause an audible and/or tactile feedback to the user.

In a normal operation mode the drive member 20 is rotationally locked with the piston rod 12 by means of splines, which enables only axial movement between the drive member 20 and the piston rod 12.

To reset the drive mechanism the piston rod 12 must be returned in the proximal direction back into the housing. This is impossible when the drive mechanism is engaged. The piston rod 12 has to rotate through the threaded engagement to the housing. The drive member 20 is splined to the piston rod 12 and would also rotate. The stop member 26 stops the drive member 20 from rotating. During reset the drive member 20 is decoupled from the piston rod 12, so that the piston rod 12 can rotate back to an initial start position.

Figure 4:
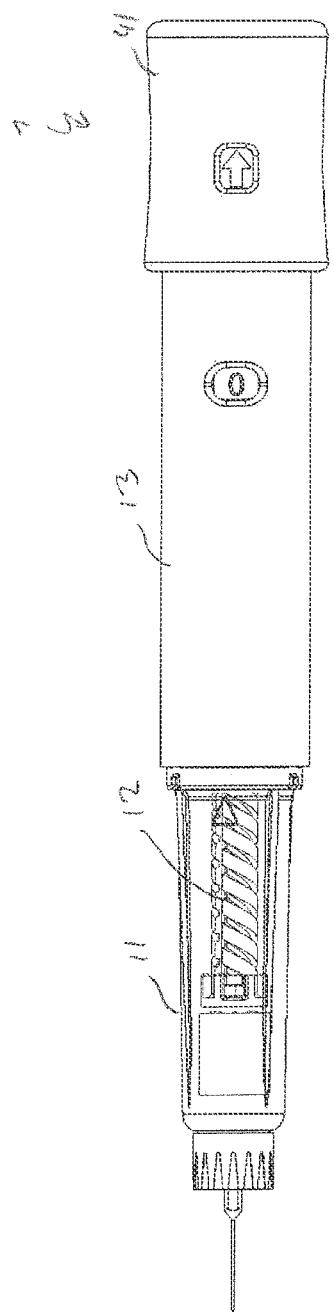
FIGS. 4 to 6 show side views of the drug delivery device during cartridge change.
Figure 5:
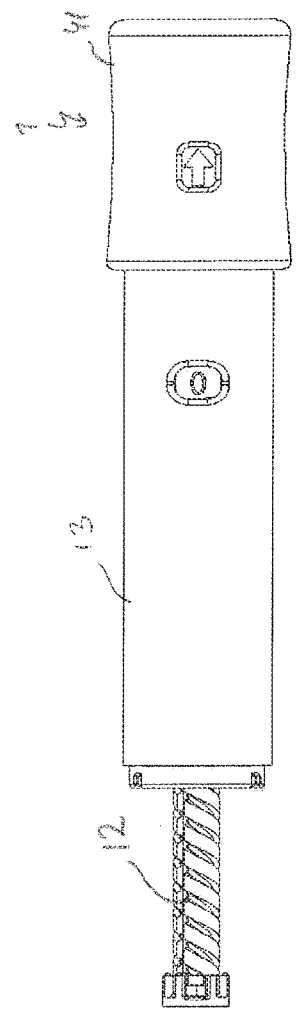
Figure 6:
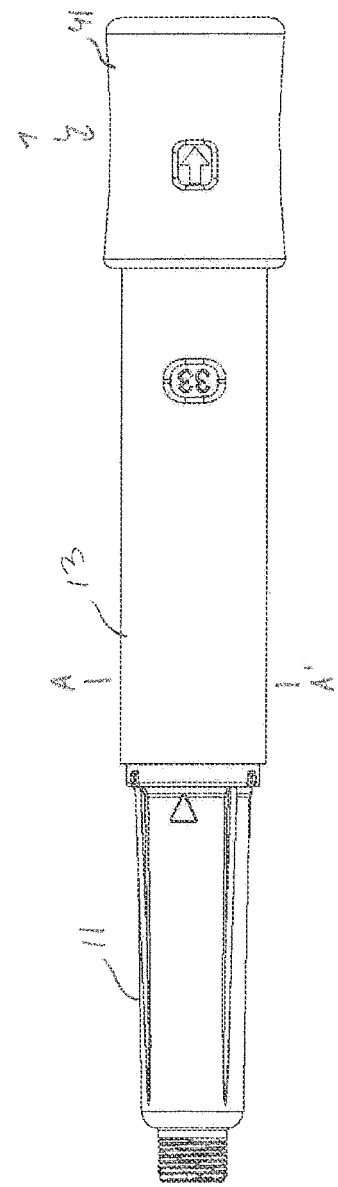

FIG. 4 shows the device and in particular the position of the piston rod 12 after delivery of the last dose. FIG. 5 shows this device after detaching the cartridge holder 11. When the cartridge holder 11 is detached, the piston rod 12 is decoupled from the drive member (not shown in FIGS. 4 to 6). FIG. 6 shows the device after returning the piston rod 12 to its initial start position and attaching a new cartridge. In this mode the drive member is splined to the piston rod again.

Figure 7:
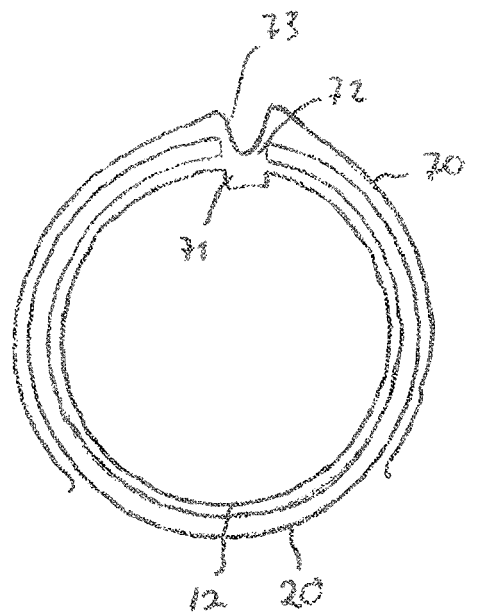
FIG. 7 shows a sectional view of a part of one embodiment of the drive mechanism in a reset operation mode.

FIG. 7 shows a sectional view along line AA' in FIG. 6 of one embodiment of a part of a drive mechanism in the reset mode. Only the drive member 20, the piston rod 12 and a spring 70 which is suitable to spline the drive member 20 to the piston rod 12 is shown. In the reset mode the drive member 20 and the piston rod 12 are decoupled.

The piston rod 12 comprises a first track 71 which extends in the axial direction. The track may be the engagement track 37 shown in FIG. 3. The drive member 20 comprises a second track 72 formed as a hole. The spring 70 runs partly circumferentially around the drive member 20. The spring 70 has a protruding part 73 which is suitable to be pushed through the second track 72 of the drive member 20 into the first track 71 of the piston rod 12 so that the drive member 20 and the piston rod 12 cannot rotate with respect to each other. In other words, the protruding element 73 may serve as a spline. However, axial movement is still possible. The protruding part 73 may slide along the first track 71. In the reset mode the spring 70 is relaxed so that protruding element 73 is pulled out off at least the first track 71, thereby the piston rod 12 being rotatable with respect to the drive member 20, which enables to reset the device. The protruding element 73 may be integrally formed with the spring, e.g. as v-shaped or u-shaped part of the spring 70. Alternatively the protruding element 73 may be a pin-like element attached to the spring 70.

The spring 70 relaxes so that the protruding element 73 is moved radially outwards, when the cartridge holder (not shown in FIG. 7) is detached. The disengagement enables to rotationally move the piston rod 12 in the proximal direction, while the drive member 20 does not rotate with respect to the housing 17.

Figure 8:
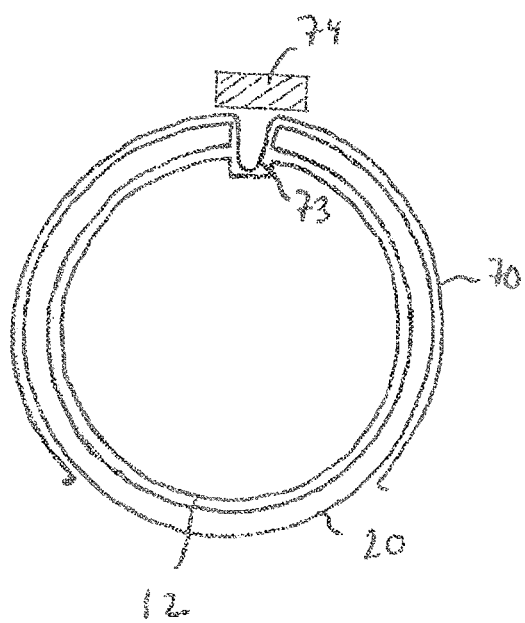
FIG. 8 shows a sectional view of the part of the embodiment of FIG. 7 in a normal mode.

FIG. 8 shows a sectional view of the embodiment shown in FIG. 7 in the normal operation mode, in which the protruding element 73 extends through the second track 72 of the drive member 20 into the first track 71 of the piston rod 12, thereby coupling the drive member 20 and the piston rod 12 so that they cannot rotate with respect to each other.

The spring 70 is deformed so that the protruding element 73 is pushed radially inwards when the cartridge holder is attached. The cartridge holder may be formed so that the spring 70 is deformed and couples the drive member 20 and the piston rod 12 when the cartridge holder is attached. In one embodiment the cartridge holder comprises a radially inwards extending protrusion 74 serving as a push member which pushes the protruding element radially inwards when the cartridge holder is attached. In another embodiment the cartridge holder pushes an element of the device so that the spring 70 is deformed. Alternatively, the drive member 20 slides away from the push member which may be part of the housing 17, when the cartridge holder is detached. This movement may be caused by a relaxing spring element.

Figure 9:
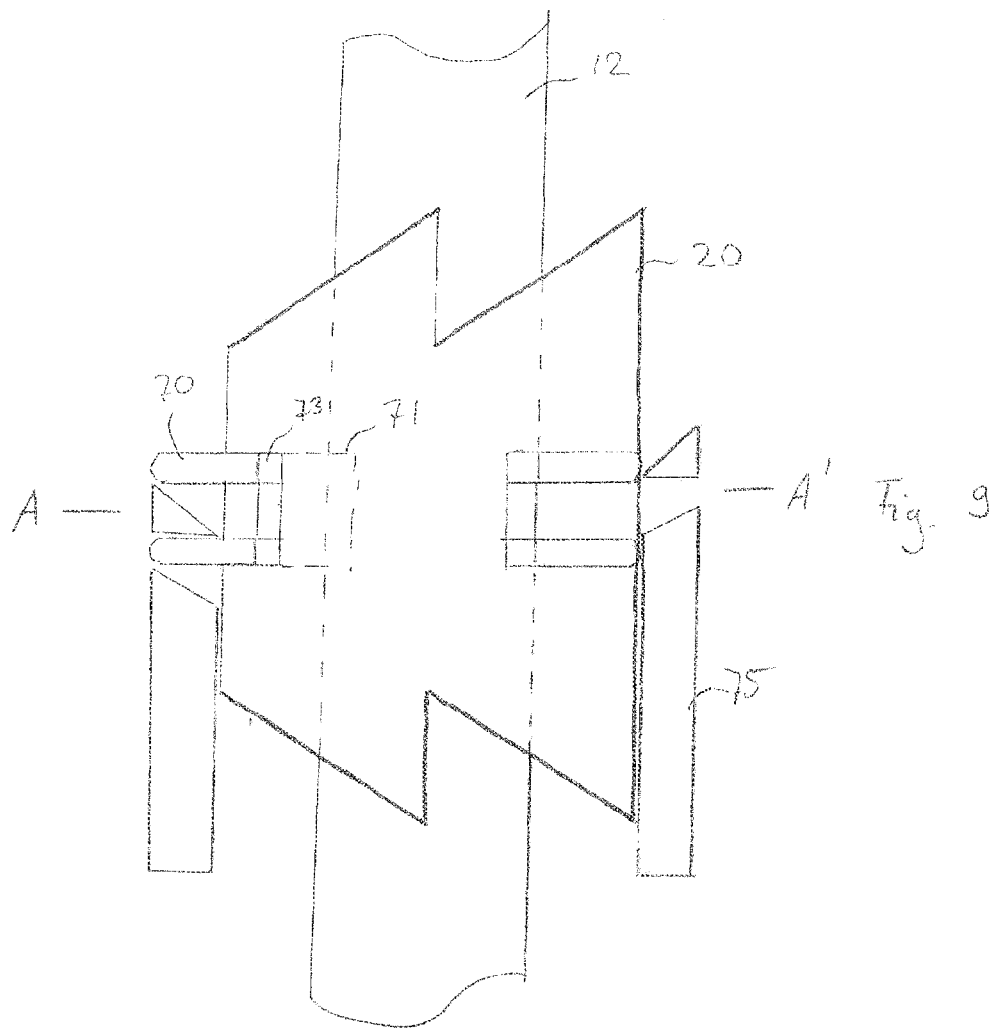
FIG. 9 shows a side view of a part of another embodiment of the drive mechanism.
Figure 10:
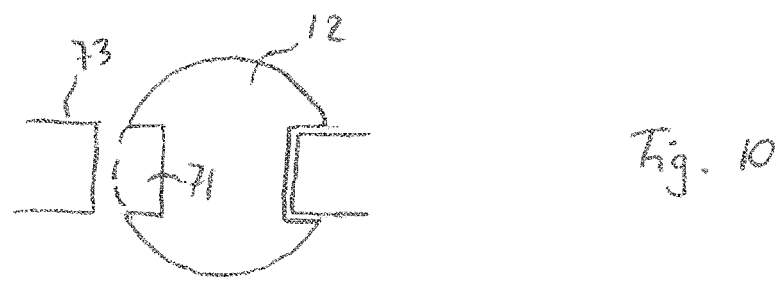
FIG. 10 shows a sectional view of the part of the embodiment of FIG. 9.

FIGS. 9 and 10 show a further embodiment wherein a spring 70 is running partly circumferentially around the drive member 20, the spring 70 comprising protruding elements 73. In this embodiment the protruding elements 73 are formed as inwardly extending ends of the spring 70. The piston rod 12 comprises axially running first tracks 71 which are arranged on opposite sides of the piston rod 12. The drive member 20 comprising second tracks formed as holes on opposite sides of the drive member 20, the first and second tracks are aligned. Push means 75 are provided which are suitable to deform the spring 70 so that the protruding elements 73 engage with the tracks in the drive member 20 and the piston rod 12. The push members 75 may be parts of the cartridge holder, which slides along the spring 70 so that it deforms during attachment, as shown on the right hand side of FIG. 9. During the detachment of the cartridge holder the push members 75 are moved away from the spring 70 so that it relaxes and the protruding elements disengage, as shown on the left hand side of FIG. 8. The distal parts of the push elements 75 may be sloped which avoids blocking during attachment and enables sliding of the push elements 75 over the spring 75 during attachment. The left hand side of FIG. 10 shows a protruding element 73 which is disengaged from the first track 71 in the piston rod 12. The right hand side of FIG. 10 shows a protruding element 73 which is engaged with the first track 71.

FIG. 11 shows an exploded view of a further embodiment, comprising a housing 17, a piston rod 12, a stop member 26 and a drive member 20. FIGS. 12A and 13A show the embodiment in sectional views in the normal operation mode and the reset mode, respectively.

The drive member 20 is positioned inside the housing 17 which comprises a part formed as a sleeve 96 and is suitable for guiding the drive member 20, the sleeve 96 having a circumferential trench 99.

The piston rod 12 comprises at least one axially extending track 71, preferably more than one. Pegs 91 are provided for releasably coupling the drive member 20 and the piston rod 12 by means of a splined connection. The peg 91 comprises a coupling part 92 which is suitable for engaging with the track 71 and a shaft 97 having a head 93, wherein the diameter of the shaft 97 is less than the one of the head 93. The shaft 93 is put through a hole 94 in the drive member 20. The hole 94 has a size and form that corresponds with the section of the shaft 97 but avoids movement of the head 93 and the coupling part 92 through the wall of the drive member 20. The radial movement of the peg 91 with respect to the drive member 20 is limited by the head 93 which is located outside the drive member 20 and the coupling part 92 which is located inside the drive member 20. A leaf spring 95 is located on the outer side of the drive member 20; the leaf spring 95 having a hole 98. The leaf spring 95 is positioned in a cavity 89 of the drive member 20. The leaf spring 95 is curved in a relaxed state. The contour of the cavity 89 corresponds with the even form of the leaf spring 95 under compression. The hole 94 of the drive member 20 and the hole 98 of the leaf spring 95 are aligned. The shaft 97 of the peg 91 extends through the holes 94, 98 so that the coupling part 92 is located inside the drive member 20 while the head 93 is located outside. When the leaf spring 95 is relaxed the peg 91 is biased outwardly, so that the head 93 and the coupling part 92 are pushed radially outwards. When the head 93 is pushed inwards the leaf spring 98 is deformed by the underside of the head 93 which pushes onto the leaf spring 95; thereby moving the coupling part 92 radially inwards so that it engages with the track 71. The position of the pegs 91 is aligned with the position of the tracks 71.

FIG. 12A shows the embodiment of FIG. 10 in a sectional view. FIG. 12B is a detailed view of a marked part of FIG. 12A. FIG. 12C shows the arrangement of the peg 91 in detail. FIGS. 12A, 12B and 12C show the drive mechanism in the normal operation mode, which means that the drive member 20 and the piston rod 12 are coupled.

In the normal operation mode there is a gap 85 between the housing 17 and the stop member 26 which is held apart from the housing 17 by a spring member (not shown). The spring member pushes the stop member 26 proximally when the cartridge holder is attached. The stop member 26 forces the drive member 20 to a position in which the heads 93 of the pegs 91 are not aligned with the trench 99. In other words, the sleeve 96 which serves as push means 75 pushes the pegs 91 radially inwards, so that the coupling parts 92 engage with the tracks 71 in the piston rod 12. The heads 93 are positioned in the cavities 89 and do not or only slightly protrude from the outer side of the drive member 20.

FIG. 13A shows the embodiment of FIG. 11 in a sectional view. FIG. 13B is a detailed view of a marked part of FIG. 13A. FIG. 13C shows the arrangement of the peg 91 in detail. FIGS. 13A, 13B and 13C show the drive mechanism in the reset mode, which means that the cartridge holder is detached. After detachment the stop member 26 and the drive member 20 move distally with respect to the housing 17. When the heads 93 of the pegs 91 reaches the trench 99, the leaf spring 95 relaxes so that the heads 93 protrude from the drive member 20 into the trench 99, thereby moving the coupling parts 92 towards the inner side of the drive member 20. When the pegs 91 move radially outwards, the coupling parts 92 disengage from the tracks 71 in the piston rod 12 so that the drive member 20 and the piston rod 12 can rotate with respect to each other which enables resetting the device.

FIGS. 14A, 14B, 14C show another embodiment of a drive member 20 having pegs 91. FIG. 14A shows a three-dimensional view. FIG. 14B shows a sectional view. FIG. 14C shows an exploded sectional view.

The pegs 91 are u-shaped. Each peg 91 has a coupling part 92 and two shafts 97 with heads 93 protruding at the ends of the coupling part 92. An alternative embodiment of the peg (not shown) comprises more than two shafts. The shafts 97 extend through holes 94 in the drive member 20. A resilient member biases the peg 91 outwardly. A spring coil 88 runs around each shaft 97 between the outer side of the drive member 20 and the head 93. The holes 94 are located in a cavity 89 so that the heads 93 do not protrude from the outer side of the drive member 20 if the heads 93 are pushed radially inwards.

FIGS. 15A and 15B, which is more detailed, show a sectional view of the drive member 20 of FIGS. 14A, 14B, 14C in the normal operation mode. When the cartridge holder is attached, the sleeve 96 serving as push means 75 pushes onto the heads 93 of the pegs 91 so that coupling part 92 engages with the track 71 in the piston rod 12.

FIGS. 16A and 16B, which is more detailed, show a sectional view of the drive member 20 of FIGS. 14A, 14B, 14C in the reset state. After detaching the cartridge holder the drive member 20 moves axially with respect to the sleeve 96 so that the heads 93 reach the trench 99 in the sleeve 96. Then the spring coils 88 relax, thereby pushing the heads 93 radially outwards into the trench 99. This movement causes disengagement of the coupling parts 92 from the track 71 in the piston rod 12 which enables rotational movement of the piston rod 12 with respect to the drive member 20 for the purpose of resetting the piston rod 12.

It should be mentioned that the features of the embodiments can be combined.

The invention claimed is:

1. A drive mechanism for a drug delivery device which can be switched between a normal operation mode and a reset mode, the drive mechanism comprising
    a housing having a proximal end and a distal end;
    a piston rod which is adapted to be displaced in a distal direction with respect to the housing for delivering a dose in a normal operation mode of the drive mechanism, and which is adapted to be displaced in the proximal direction with respect to the housing in a reset mode of the drive mechanism;
    a retractable spline connection that releasably engages the piston rod in the normal operation mode and disengages the piston rod in the reset mode;
    a drive member which is rotationally moveable in a rotation direction with respect to the housing, wherein, in the normal operation mode, the drive member is rotationally locked with the piston rod through engagement of the retractable spline connection so that rotational movement of the drive member in the rotation direction with respect to the housing is converted into movement of the piston rod in the distal direction with respect to the housing yet allowing axial movement between the drive member and the piston rod, and wherein, in the reset mode, the piston rod is decoupled from the drive member by retraction of the spline connection; and
    a stop member configured to prevent rotational movement of the drive member relative to the housing during dose setting and to allow the the drive member to rotate with respect to the stop member during dose delivery,
    wherein, in the normal operation mode, the drive member is splined to the piston rod such that the drive member cannot rotate relative to the piston rod and rotational movement in the rotation direction of the drive member with respect to the housing is converted into rotational movement of the piston rod in the same direction, and in the reset mode the piston rod being rotatable with respect to the drive member for displacing the piston rod in the proximal direction.

2. The drive mechanism according to claim 1, wherein the drive member which has an inner side facing the piston rod and an outer side facing away from the piston rod comprises a spring, in the normal operation mode the spring protrudes inwardly and engages with a track in the piston rod, and in the reset mode the spring protrudes outwardly.

3. The drive mechanism according to claim 2, wherein the spring is biased outwardly.

4. The drive mechanism according to claim 3, wherein the spring has a protruding element which engages the drive member and the piston rod in the normal operation mode, thereby splining the drive member to the piston rod.

5. The drive mechanism according to claim 4, wherein the drive member has a track and the piston rod has a track, the protruding element engaging with the tracks in the normal operation mode.

6. The drive mechanism according to claim 5 further comprising a push member configured to move into a position so that it pushes the protruding element in the tracks of the drive member and the piston rod.

7. The drive mechanism according to claim 4, wherein the protruding element is biased outwardly so that the drive member is rotatable with respect to the piston rod in the reset mode, the spring being biased out of engagement in the reset state.

8. The drive mechanism according to claim 3, further comprising a push member which is moved to a position so that it pushes the spring inwardly when the drive mechanism is switched to the normal operation mode.

9. The drive mechanism according to claim 3, further comprising a push member, wherein the drive member is moved with respect to the push member so that the push member pushes the spring inwardly when the drive mechanism is switched to the normal operation mode.

10. The drive mechanism according to claim 1 suitable for being releasably connected with a cartridge holder, wherein the drive mechanism is switched to the reset mode when the cartridge holder is detached from the drive mechanism.

\* \* \* \* \*